United States Patent [19]

Trumble

[11] 3,982,130

[45] Sept. 21, 1976

[54] ULTRAVIOLET WAVELENGTH SMOKE DETECTOR

[75] Inventor: Terry M. Trumble, Dayton, Ohio

[73] Assignee: The United States of America as represented by the Secretary of the Air Force, Washington, D.C.

[22] Filed: Oct. 10, 1975

[21] Appl. No.: 621,338

[52] U.S. Cl............................ 250/373; 340/237 S; 356/51; 356/205; 356/207
[51] Int. Cl.²................... G01N 21/12; G01N 21/26
[58] Field of Search ............ 250/373; 356/207, 104, 356/205, 51; 340/237 S

[56] References Cited
UNITED STATES PATENTS

| | | | |
|---|---|---|---|
| 2,369,966 | 2/1945 | Hawkins | 250/373 |
| 3,770,356 | 11/1973 | Kimura | 356/207 |
| 3,857,641 | 12/1974 | Gass | 356/207 |

*Primary Examiner*—Alfred E. Smith
*Assistant Examiner*—T. N. Grigsby
*Attorney, Agent, or Firm*—Joseph E. Rusz; Robert Kern Duncan

[57] ABSTRACT

Collimated ultraviolet light radiation at wavelengths of 2537A and 3129A is alternately directed across the space to be monitored for smoke indicative of a fire. A "cats eye" mirror at the far side of the monitored space returns the ultraviolet rays to a photomultiplier detector adjacent the light source. Smoke, for example pine smoke having a particle mean diameter of 1.4 to 3.0 micrometers, will attenuate the shorter wavelength beam much more than the longer wavelength beam. Approximately 1.3 times greater attenuation is inflicted on the 2537A beam than on the 3129A by the pine smoke. Thus, returning beam signals having this ratio of signal levels will provide an indication of a pine fire. Particles of a different diameter intercepting the beam will produce a different ratio of attenuated signals.

4 Claims, 4 Drawing Figures

ULTRAVIOLET WAVELENGTH SMOKE DETECTOR

RIGHTS OF THE GOVERNMENT

The invention described herein may be manufactured and used by or for the government of the United States for all governmental purposes without the payment of any royalty.

BACKGROUND OF THE INVENTION

The field of the invention is in the smoke and atmospheric particle detection art.

Many types of smoke detecting devices are known. Some simple devices merely utilize the attenuation of a light beam for an indication that smoke or some particulate matter has intercepted the beam. More sophisticated devices use a forward scattering effect measured in a labyrinth. U.S. Pat. No. 3,860,818 to patentees Stalder et al is an example of a typical atmospheric monitor. Some state of the art devices use high power laser beams. They are very satisfactory smoke detectors but generally they are hazardous to personnel.

SUMMARY OF THE INVENTION

Collimated low intensity ultraviolet light radiation at two different wavelengths, both wavelengths shorter dimensionally than the smoke particle diameters to be detected, are alternately projected across the space to be monitored. Particulate matter in the beam paths will effect the different wavelengths with different amounts of attenuation. The ratio of the attenuated beams is indicative of the size of the particulate matter in the beam paths. The invention provides a smoke/fire detector that operates at a level that will not injure human eyes. It operates over an open path and thus has fast response (approximately one minute); it is reliable and particle selective, and by not being sensitive to equipment alignment or vibratory movement, it is easy to install. It also monitors its own out of tolerance condition to provide "fail" indication.

DESCRIPTION OF THE PREFERRED EMBODIMENT

Figure 1:
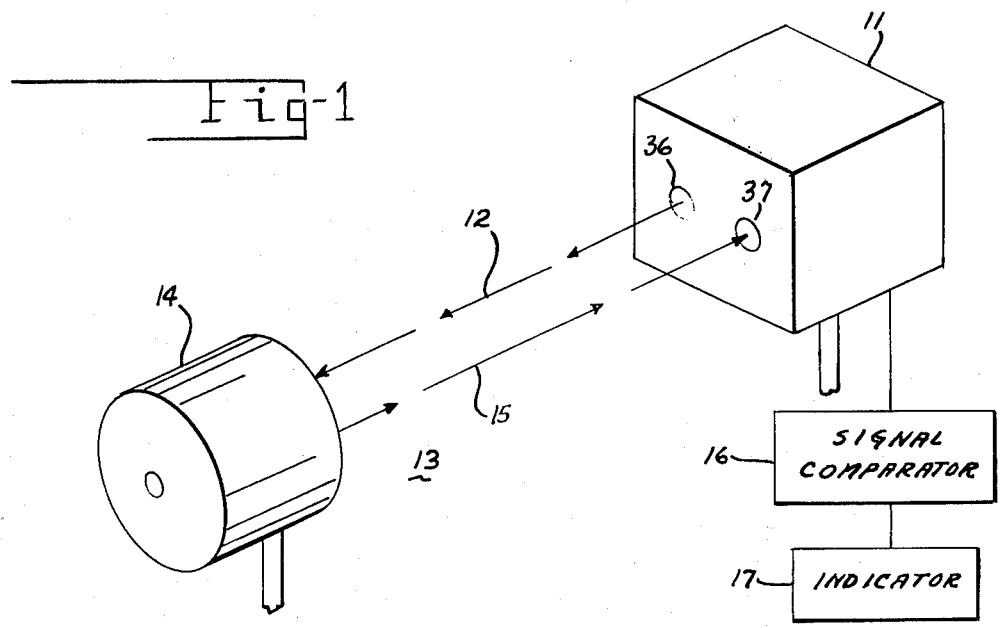
FIG. 1 is a block-pictorial representation of an embodiment of the invention.

FIG. 1 is a pictorial representation of an embodiment of the invention. The source/detector unit 11 contains the ultraviolet source providing alternate beams of 2537A wavelength and 3129A wavelength radiation, through the general location 13 to be monitored for a fire by detecting the presence of smoke, to the cats eye retroreflector 14. The alternate wavelength beams are reflected 15 by the cats eye back to a photomultiplier detector tube in the source/detector unit 11. While the beam 12 is substantially a collimated beam, it does spread and at the location of the cats eye 14 it floods, i.e., overfills, the reflecting surface of the corner cube in the cats eye which in turn, at the detector, overfills the phototube photocathode. By making the flooding or overfilling approximately 2 to 1 at both locations the system becomes quite insensitive to alignment and vibration with a fixed nominal loss in sensitivity. The output levels of the two beams from the photodetector are compared by the signal comparator 16 and the ratio of the levels of the intensity of the two beams after they have traversed the location 13 is indicative of the size of any particulate matter intercepting the beam paths 12 and 15. If this signal ratio is the value of a predetermined number indicative of the smoke from a fire the indicator 17 provides a visual or auditory alerting signal. If a ratio of signal levels occurs in the comparator 16 that would not be a representation of particulate matter an indication is provided by the indicator 17 to indicate a system failure.

Figure 2:
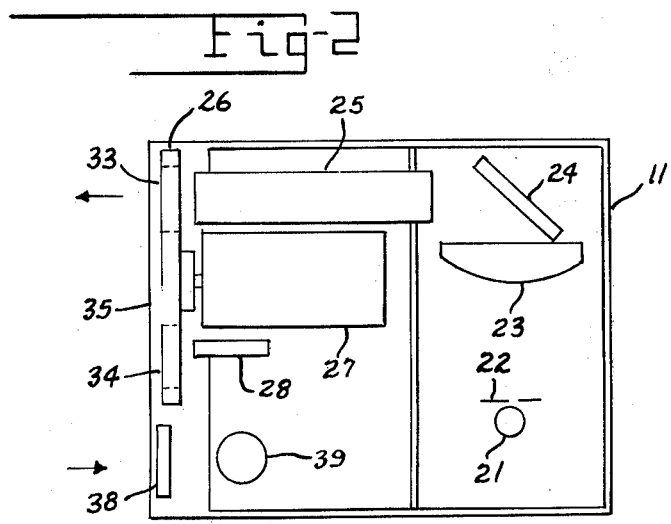
FIG. 2 is a schematic-pictorial representation of a typical source/detector unit with the top cover removed.
Figure 3:
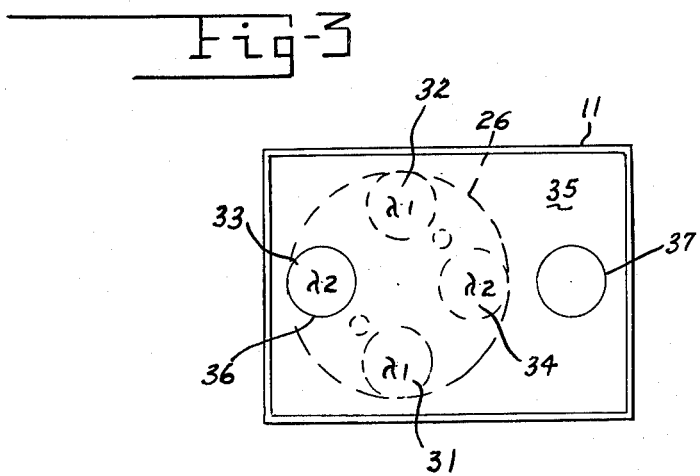
FIG. 3 is a schematic-pictorial representation of a front view of a typical source/detector unit.

FIG. 2 illustrates the interior of a typical source/detector unit, and FIG. 3 is illustrative of a typical front view of the unit. A small, conventional, commercially available HgNe lamp 21 provides the source of ultraviolet radiation. The radiation from the lamp passes through the conventional pinhole point source determining baffle 22 and is collimated by a convention suprasil quartz double-convex lens 23. Mirror 24 directs the radiation through the light-shield tube 25 and through the rotating chopper wheel 26 driven by motor 27. The chopper wheel has two sets of filter disks 31 and 32 for $\lambda_1$ and 33 and 34 for $\lambda_2$. Filters 31 and 32 pass substantially only ultraviolet radiation having a wavelength $\lambda_1$ of 2537A. Filters 33 and 34 pass substantially only ultraviolet radiation having a nominal wavelength $\lambda_2$ of 3129A. The nominal 3129A wavelength is actually a doublett, 3126A and 3132A combined. Both of these wavelengths are abundantly available from the conventional mercury lamp 21. The nominal power input to the mercury vapor lamp 21 is set at approximately 10 watts. The dosis limit of ultraviolet radiation for personal safety is generally accepted to be $0.1 \times 10^{-6}$ watts per square centimeter. This will not be exceeded by embodiments of the invention operated at the stated foregoing input power level, and it will be safe for humans to look into the ultraviolet beam and to have their skin exposed to the beam.

The preferred, although not critical, speed of rotation of the chopper wheel 26 containing the filters 31 through 34 is approximately 2200 rpm. Magnetic pickup sensor 28 conventionally detects the rotational speed of the wheel and furnishes pulses for the timing gates in the electronic circuitry. The front 35 of the case 11 of the source/detector unit has openings 36 and 37 for egress and ingress respectively, of the beams. A fixed low pass (i.e., short wavelength) optical filter 38 cuts off radiation greater in wavelength than the upper wavelength beam utilized by the equipment from entering the photomultiplier photodetector tube 39. Thus, the effects of artificial electric lighting is minimized. (An additional electronic filter later described also aids in this discrimination.)

Figure 4:
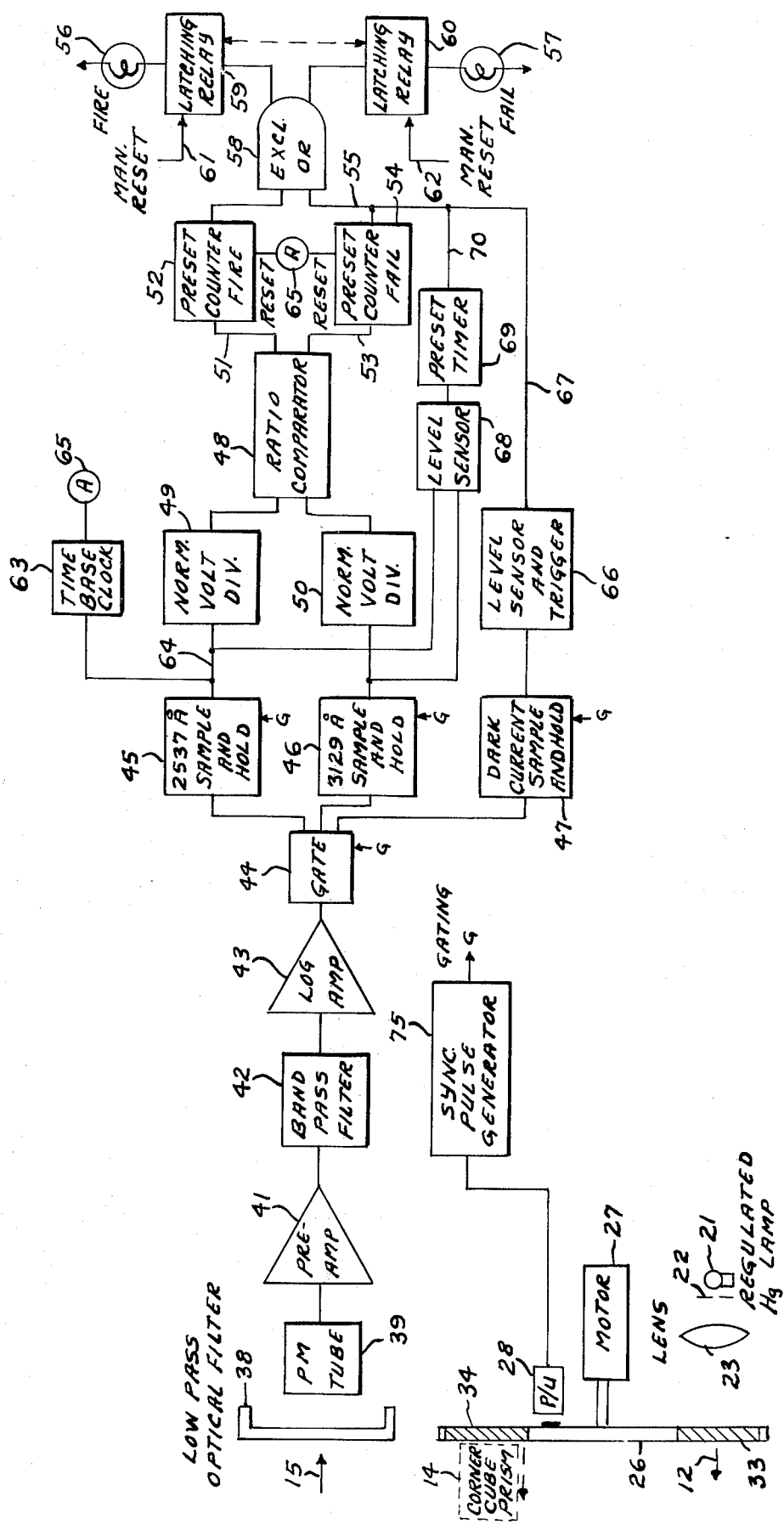
FIG. 4 is a schematic-block diagram of a typical embodiment of the invention.

The details of the electronic circuitry of the system are shown in block-schematic form in FIG. 4. To aid in the practicing of the invention its operation will be described in the following step-by-step process. The conventional ultraviolet sensitive photomultiplier detector tube 39 is conventionally operated on a regulated direct current supply. The output signal from the detector consists of a series of pulses originating from the rotation of the chopper wheel 26 and its filters interrupting the radiation from the mercury lamp 21..

This series of pulses is amplified by preamplifier 41 to a suitable level for the bandpass filter 42 and the logarithmic amplifier 43. The bandpass filter 42 is centered on the returning light pulse frequency arriving at the phototube 39. This greatly aids in making the system nonresponsive to extraneous illumination such as fluorescent lights. In the embodiment being described the light from the lamp is chopped four times per revolution of the chopper wheel 26. With the chopper wheel revolving at 2200 rpm this amounts to a 146.6 hz signal on the phototube. By making narrow bandpass filter 42 a filter 10 hz wide centered on 146.6 hz the effects of fluorescent lights which are flickering at 120 hz are virtually eliminated.

The logarithmic amplifier 43 is required to compress the 4 to 6 decade range of the photomultiplier detector tube into approximately one decade so the range of levels can be easily handled by conventional electronics. In some specific installations of the invention it may not be necessary to use a logarithmic amplifier, however, it is generally desirable as it makes it possible for the system to detect and discriminate smoke from very low optical density levels to very high optical density levels. The gate circuit 44 is controlled by the synchronous pulse generator 75 so that the signal being received at the photomultiplier detector tube is gated to the appropriate hold circuit corresponding to the wavelength of the radiation being passed at that instant by the filter in the chopper wheel.

The sync pulse generator 75 in addition to controlling the gate 44 for switching the correct $\lambda_1$, $\lambda_2$ received signals into the respective sample and hold circuits 45 and 46, also gates the level when no radiation is being emitted from the source/detector unit, by reason of no opening being in front of the mercury lamp, to provide a dark current level for the dark current sample and hold circuit 47. (This dark current level is actually the ambient light level.) Thus, the gate 44 through its timing function provides the level of the 2537A signal to hold circuit 45, the level of the 3129A signal to hold circuit 46, and a dark current signal level to hold circuit 47. Timing pulses from the pulse generator 45 also gates the outputs from the hold circuits 45, and 46 so that the representative stored voltages are impressed simultaneously on the ratio comparator 48.

The sample and hold circuits 45, 46, and 47 are conventional electronic circuits. They store the signals as they arrive in time sequence. After the signal levels have been stored a sync pulse from generator 45 simultaneously gates the representative signal levels out of the sample and hold circuits. This occurs once every half cycle of the optical chopper wheel 26.

The normalization circuits 49 and 50 provide for an initial manual adjustment of unattenuated (clear path) 3129A and 2537A signals to make them equal in signal voltage level as presented to the ratio comparator 48. That is, a 1/1 ratio for unobstructed ultraviolet beam paths. It is generally preferred to initially normalize the signals before comparison so that the signal ratio departs from the 1 to 1 ratio with no particulate matter in the beam paths, to some other ratio depending upon the particulate size present in the beams. (Note that dust, for example will attenuate both beams approximately the same amount and thus will not appreciably change the ratio.) Normalization, while preferred, is not a requirement. By using a more complex ratio comparator circuit 48, the system can be made to operate satisfactorily with absolute values of input signal, and provide a signal representative of the departure of the new ratio from the unobstructed ratio. Operation and construction is simplified with normalization so that the ratio comparison circuit provides no output when the ratio of the 3129A signal to the 2537A signal is 1 to 1. As previously stated the ratio of signals for pine smoke is approximately 1.3 to 1 and thus for detection of a fire from pine materials the conventional ratio comparator 48 is manually set to provide an output signal when this ratio occurs. (If, for example, it is desired to detect smoke from burning mosite sponge insulating material, the ratio comparator is set to provide an output signal when the ratio of signals is approximately 1.2 to 1.) Obviously, there is some overlapping of the ratios of common combustible materials such as are found in building and spacecraft construction. The invention may be peaked in the ratio comparison circuits to discriminate different fires by their combustion particle size, or the system may be only broadly peaked in the ratio comparator circuit so that smoke of a general nature with particle sizes varying such that ratio of signals from approximately 1.2 to 1 to 1.6 to 1 will provide an output signal indicative of a fire. The ratio comparator thus provides an output signal on line 51 to the preset fire counter 52 whenever the predetermined signal ratio exists for that pair of pulses. (A one to one ratio provides no signal output.) In addition the ratio comparator will provide an output signal on line 53 when any signal ratio outside of the predetermined fire range (such as 1.2 up to 1.6 to 1) occurs and when any signal below 1 to 1 (such as 1 to 2) occurs. These signals are counted by the fail counter 54.

With the optical chopper 26 running at 2200 rpm it is possible within one minute to accumulate 4400 counts of 2537A or 3129A signal. Thus, for summing counts over a one-minute interval (the preferred interval), the counters 52 and 54 could each accumulate up to 4400 counts. It has been determined that a suitable number of counts in a one-minute interval to accurately and reliably indicate a fire is in the range of 1000 to 2000 counts. 1500 counts is an ideal nominal design value to set into the equipment. It has been found that a range of counts between 200 and 800 in any one-minute interval to the fail counter 54 is a suitable number to reliably indicate a failure of the system. Thus, the preset fail counter will provide an output signal on line 55 after this condition is met.

It is not desirable that both a fire and a fail indication occur at indicators 56 and 57 at the same time. To prevent this occurrence the outputs from the preset fire and fail counters are fed through the exclusive or gate 58 to mechanically coupled latching relays 59 and 60. Whichever indication occurs first excludes the operation of the other. Once either a fire or a fail indication is indicated by indicator 56 or 67 that particular indicator stays on and the other indication can't occur until the manual reset button 61 or 62 is pushed resetting the latched relay. This mode of operation is highly desirable since it frequently happens that after a fire has progressed, failure would then be indicated due to beam blockage and material equipment destruction, thus once the fire indication is made, it stays on until manually removed.

The time base clock 63 determines the sampling period. As previously indicated, one minute is the preferred time base over which to sum indications. It is not critical and other time intervals may also be used. When a signal on line 64 is received from the 2537A sample and hold 45 the time base clock 63 is initiated. It continues to run for a predetermined interval (one minute preferred). At the end of the interval the clock puts out a clear signal through connection 65 to reset both the present fire and preset fail counters 52 and 54. If these counters have not reached their full count (which sends a signal to the exclusive OR circuit 58) by the end of the minute, they are cleared and they immediately start counting again on the receipt of any input signals.

The dark current sample and hold circuit 47 senses and stores the level of the ambient light output from the photomultiplier detector tube when no ultraviolet light is emitted from the source, i.e., a blank spot on the chopper wheel 26 is intercepting the light from the mercury lamp 21. If this voltage level increases more than a nominal 50% over the normal expected ambient light level set in the level sensor 66, a schmidt trigger circuit fires and initiates a voltage output signal on line 67 that activates the fail indicator 57.

If either or both of the signals from line 2537A and the 3129A sample and hold circuits 45 and 46 drops below a predetermined value of signal (typically $1 \times 10^{-3}$ of the unobstructed beam signal), which indicates either a total or nearly total ultraviolet optical beam blockage, the level sensor 68 provides a signal initiating the preset timer circuit 69. One minute has been found to be an optimum time interval to set in the timer circuit 69. Any time the beam is cleared and nominal signal levels of ultraviolet radiation are received by the detector tube in the one-minute interval after interruption, the timer is turned off and reset ready to be initiated at the next beam blockage. If the timer is not turned off and the timer continues to run for a full minute, indicating that the beam has been blocked for this time, the timer then initiates a signal on line 70 that progresses through the exclusive OR gate and turns on the fail indicator 57.

The ultraviolet frequencies of 2537A and 3129A are generally preferred, due to ease of generation and detection, but they are not critical. The primary requirement is that the light radiation used be shorter in wavelength than particle mean diameter to be detected. In the specific embodiment of the invention described in detail, primarily for pine smoke detection, the specific frequencies enumerated are approximately a decade shorter in wavelength than the particle mean diameter of pine smoke. The low pass optical filter 38 attenuates radiations of longer wavelengths than the longer wavelength beam used, in this embodiment wavelengths longer than 3129A, allowing most of the 3129A and 2537A radiation to pass through the filter to the detector tube. For embodiments using other wavelengths the cutoff of this filter is changed accordingly. Another reason why these specified wavelengths are generally preferred is that at sea level almost no radiation exists below 2900A in wavelength. Thus, the 2537A wavelength is quite insensitive to solar radiation and the 3129A nominal wavelength is only slightly sensitive to sunlight. Also, these wavelengths are predominant lines in the emission spectrum of conventional ultraviolet lamps. All of the electronic circuits used in the invention are conventional and well known, and throughout the complete structure of the invention no separate, individual, components, structures, or circuits, are unique. It is the combination of these well known elements into a unique system, functioning in a new manner to provide a new and improved smoke detector that constitutes the invention.

I claim:

1. A system for detecting, at a location, smoke having a determined suspended particulate means diameter size comprising:
    a. An ultraviolet source providing a first ultraviolet radiation beam at a first ultraviolet wavelength and a second ultraviolet radiation beam at a second ultraviolet wavelength;
    b. means for directing said first and said second ultraviolet beams successively to traverse the said location;
    c. means for detecting the respective signal levels of the said first and the said second beams after they have traversed the said location, and providing a signal proportional to each of the respective signal levels of each beam;
    d. means responsive to the said signal level of each beam for providing an output signal when the ratio of the said signal levels is a determined value indicative that said particulate mean diameter particles are present in the said beams; and
    e. means cooperating with the said output signal for providing an indication.

2. The system as claimed in claim 1 wherein the said first and the said second ultraviolet wavelengths are shorter in length than the said particulate mean diameter.

3. Apparatus for detecting pine smoke at a determined location comprising:
    a. means for generating a 2537A beam;
    b. means for generating a 3129A beam;
    c. means for chopping and successively and repetitively radiating the said beams through the said determined location;
    d. means for detecting the intensity levels of the said beams after traversing the said location and providing a first output voltage responsive to the detected level of the said 2537A beam and a second output voltage responsive to the detected level of the said 3129A beam;
    e. means including a ratio comparator for providing a third output signal when the ratio of the said output level of 3129A beam to the said 2537A beam is approximately 1.3 to 1;
    f. means cooperating with the said third output signal for providing an indication.

4. The apparatus as claimed in claim 3 wherein means for manually setting a ratio of 1 to 1 of said first and said second output signals in the said ratio comparator in the absence of said smoke is provided.

* * * * *